United States Patent
Jeraj et al.

(10) Patent No.: US 11,918,374 B2
(45) Date of Patent: Mar. 5, 2024

(54) APPARATUS FOR MONITORING TREATMENT SIDE EFFECTS

(71) Applicants: Wisconsin Alumni Research Foundation, Madison, WI (US); AIQ Solutions, Madison, WI (US)

(72) Inventors: Robert Jeraj, Madison, WI (US); Daniel Huff, Madison, WI (US); Timothy Perk, Madison, WI (US); Stephen Yip, Chicago, IL (US); Glenn Liu, Waunakee, WI (US)

(73) Assignees: Wisconsin Alumni Research Foundation, Madison, WI (US); AIQ Global, Inc., Madison, WI (US)

(*) Notice: Subject to any disclaimer, the term of this patent is extended or adjusted under 35 U.S.C. 154(b) by 360 days.

(21) Appl. No.: 17/236,715

(22) Filed: Apr. 21, 2021

(65) Prior Publication Data

US 2021/0345957 A1 Nov. 11, 2021

Related U.S. Application Data

(60) Provisional application No. 63/021,936, filed on May 8, 2020.

(51) Int. Cl.
| | |
|---|---|
| *A61B 5/00* | (2006.01) |
| *G06T 7/00* | (2017.01) |
| *G16H 30/40* | (2018.01) |
| *G16H 50/30* | (2018.01) |

(52) U.S. Cl.
CPC .......... *A61B 5/4848* (2013.01); *G06T 7/0012* (2013.01); *G16H 30/40* (2018.01); *G16H 50/30* (2018.01); *G06T 2207/10081* (2013.01); *G06T 2207/10088* (2013.01); *G06T 2207/10104* (2013.01); *G06T 2207/20081* (2013.01); *G06T 2207/20084* (2013.01); *G06T 2207/30096* (2013.01)

(58) Field of Classification Search
CPC ...... A61B 5/4848; G16H 50/30; G16H 30/40; G06T 7/0012; G06T 2207/10081; G06T 2207/10088; G06T 2207/10104; G06T 2207/20081; G06T 2207/20084; G06T 2207/30096
See application file for complete search history.

(56) References Cited

U.S. PATENT DOCUMENTS

| | | | |
|---|---|---|---|
| 5,365,948 A * | 11/1994 | McMichael | A61K 49/0004 128/898 |
| 2011/0060602 A1 | 3/2011 | Grudzinski et al. | |
| 2014/0276035 A1 | 9/2014 | Jeraj et al. | |
| 2016/0100795 A1 | 4/2016 | Jeraj et al. | |
| 2017/0042495 A1 | 2/2017 | Matsuzaki et al. | |

(Continued)

FOREIGN PATENT DOCUMENTS

WO 2007052634 A1 5/2007

OTHER PUBLICATIONS

International Search Report—PCT/US2021/029114—dated Aug. 17, 2021.

*Primary Examiner* — Shefali D Goradia
(74) *Attorney, Agent, or Firm* — Boyle Fredrickson, SC

(57) ABSTRACT

A system for monitoring organ health during treatment for cancer and the like makes use of physiological imaging of the kind used for treatment monitoring and organ-specific processing to provide a comprehensive assessment of treatment side-effects.

17 Claims, 3 Drawing Sheets

(56) References Cited

U.S. PATENT DOCUMENTS

| | | | |
|---|---|---|---|
| 2017/0215814 A1* | 8/2017 | Cales | G06T 7/0012 |
| 2018/0330495 A1 | 11/2018 | Jeraj et al. | |
| 2018/0344264 A1* | 12/2018 | Choi | A61K 35/18 |
| 2019/0095759 A1* | 3/2019 | Kanada | G16H 30/40 |
| 2019/0228257 A1 | 7/2019 | Karimabadi | |
| 2019/0286652 A1* | 9/2019 | Habbecke | A61B 90/37 |
| 2020/0085382 A1* | 3/2020 | Taerum | G06T 7/0016 |
| 2021/0249142 A1* | 8/2021 | Lau | G06N 3/045 |

* cited by examiner

APPARATUS FOR MONITORING TREATMENT SIDE EFFECTS

CROSS REFERENCE TO RELATED APPLICATION

This application claims the benefit of US provisional filing 63/021,936 filed May 8, 2020 and hereby incorporated by reference.

STATEMENT REGARDING FEDERALLY SPONSORED RESEARCH OR DEVELOPMENT

BACKGROUND OF THE INVENTION

The present invention relates to medical imaging equipment providing physiological imaging (e.g., PET imaging, functional MRI) and in particular to an apparatus using physiological imaging to automatically assess toxicity side-effects during treatments for cancer and the like.

Medical treatments, such as those using immunotherapy, can have side effects that are serious enough to require the treatment to be stopped. In one example, when cancer is treated using immune checkpoint inhibitors (ICI), the patient may experience immune-mediated colitis having symptoms including diarrhea. Grade 2 or 3 colitis requires holding off on ICI treatment while grade 4 colitis, which can be life threatening, requires permanently discontinuing treatment.

The impact of such side effects on treatment can be reduced by careful monitoring of the side effects during treatment. Unfortunately, the number of different possible side effects can be large and many common side effects are difficult to monitor. For example, the diagnosis of immune-mediated colitis may require a colonoscopy or biopsy of the colon, impractical for routine repeated monitoring.

SUMMARY OF THE INVENTION

The present inventors have recognized that the physiological imaging (often undertaken to monitor tumor regression during cancer treatments) can be leveraged with organ-specific toxicity rules to simultaneously provide insight into the health of uninvolved organs.

In one example, the health of the bowel can be monitored using $^{18}$F-FDG uptake, the same molecular imaging agent used to track tumors. The invention uses data from a structural imaging scanner providing anatomical information (such as a CT machine) to segment organs for focused analysis of molecular agent uptake data (such as from a PET machine) or data on organ function (such as from an MRI machine) for that organ which is applied to the toxicity rules to make organ health assessments. Multiple organs can be analyzed simultaneously to provide a comprehensive overview of organ health.

Physiological imaging as used herein refers to imaging techniques (such as PET imaging, functional MRI or MRS) that detect either molecular changes (e.g., altered metabolism), functional changes (e.g., altered blood flow) or chemical changes (e.g., regional chemical composition and absorption), in contrast to structural imaging (standard CT and MRI imaging) which provide anatomical images.

In one embodiment, the invention provides an apparatus for assessing organ health during patient treatment, the apparatus having an electronic computer executing a stored program to: (a) receive a structural image of at least one patient organ; (b) receive a physiological image of the at least one organ indicating organ function; (c) process the structural image to create a mask describing the organ; (d) use the mask to select a portion of the physiological image related to the organ; (e) apply a toxicity rule specific to the organ to the physiological image of the portion to provide an assessment of organ health, and/or (f) output an indication of organ health based on the assessment.

It is thus a feature of at least one embodiment of the invention to provide an automated system that can leverage often pre-existing physiological image information to characterize side effects that may affect treatment.

The stored program may further process the portion of the physiological image to identify lesions and refine the organ mask to remove the lesions prior to application of the toxicity rule.

It is thus a feature of at least one embodiment of the invention to allow monitoring of organ health even when the organ includes lesions being treated. By segmenting and isolating these lesions, sensitivity to organ health is increased.

The processing of the structural image to create a mask may link the mask to an organ type, and the identification of lesions in the organ may be according to lesion identification rules linked to the organ type.

It is thus a feature of at least one embodiment of the invention to provide a sophisticated quantitative analysis of uptake information with respect to organ health that would be difficult to obtain simply from observing physiological images because of the variations in how physiological images relate to organ health.

The electronic computer executing the stored program may further process the structural image to identify a lymph node region mask, the lymph node region mask being used to select a portion of the physiological scan related to lymph nodes. A lymph node activity rule may then be applied to the portion of the physiological image related to lymph nodes to assess the activity of the lymph nodes, and the output may provide an indication of lymph node activity indicating activation and/or stressing of the lymph nodes system.

It is thus a feature of at least one embodiment of the invention to provide an early measure of organ health by assessing whether the lymph nodes are being activated or overtaxed.

More generally, the stored program may provide a set of toxicity rules linked to different organs where the different toxicity rules are applied to different organs to provide assessments of organ health for multiple different organs. In this case, the output indicates organ health for multiple organs (e.g., a first and second organ; a first, second, and third organ; a first, second, third, and fourth organ, etc.).

It is thus a feature of at least one embodiment of the invention to provide the healthcare professional with a comprehensive overview of organ health that would otherwise require a prohibitive battery of tests. By automatically segmenting organs and using organ-specific rules, simultaneous assessment of organ health for multiple organs becomes practical.

The output may provide a composite measure of organ health for multiple organs.

It is thus a feature of at least one embodiment of the invention to provide the healthcare provider with an immediate indication of whether organ health has been significantly affected.

Alternatively, or in addition, the output may provide an image based on the structural image augmented with organ health data.

It is thus a feature of at least one embodiment of the invention to make use of the image data used for segmentation to provide a framework to convey the analysis of the system to the healthcare provider.

The stored program may retain previous outputs indicating organ health related to previous structural images and previous physiological images to provide a display of the trending of organ health for multiple organs.

It is thus a feature of at least one embodiment of the invention to provide important trend information that allows early response to toxicity symptoms and that would be difficult or impossible to assess with a simple viewing of individual uptake scans.

The toxicity models may include thresholds or other characteristics extracted from physiological images to predict organ health for multiple different organs and the output may indicate predicted organ health for multiple organs.

It is thus a feature of at least one embodiment of the invention to incorporate empirical understanding of current organ health to estimate likely prognosis.

The electronic computer may further analyze the physiological scan to assess change in cancerous lesions and the output may provide an indication of change in cancerous lesions.

It is thus a feature of at least one embodiment of the invention to provide an integrated display of treatment efficacy together with side effects to provide improved guidance during treatment.

These particular objects and advantages may apply to only some embodiments falling within the claims and thus do not define the scope of the invention.

DETAILED DESCRIPTION OF THE PREFERRED EMBODIMENT

Figure 1:
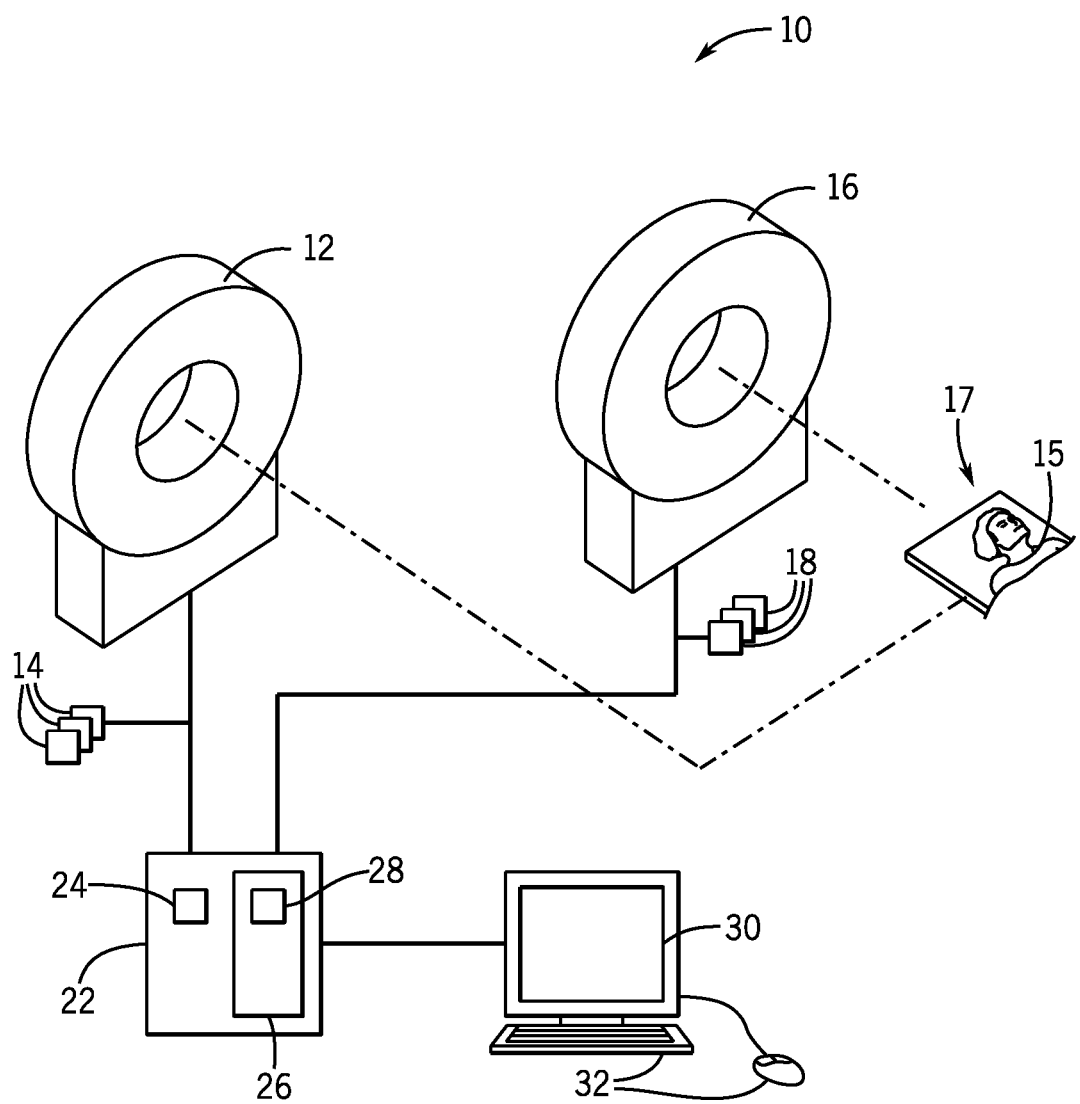
FIG. 1 is a block diagram of an example embodiment of the present invention showing a CT and PET scanner communicating with the central processor having a display terminal and executing a stored program to provide organ health information.

Referring now to FIG. 1, a system 10 for evaluating organ health during disease treatment may provide for a structural imaging scanner 12 such as a kilovoltage or megavoltage CT (computed tomography) scanner, MRI (magnetic resonance imaging) scanner or the like, which may provide for high resolution structural image scans 14 presenting anatomical information about a patient 15.

In addition, the system 10 may provide a physiological imaging scanner 16 that may scan the patient 15, for example, after introduction of a molecular imaging uptake agent 17 to measure the uptake of the uptake agent 17.

In one example, the physiological imaging scanner 16 may be a PET (positron emission tomography) scanner. As is generally understood in the art, PET is a nuclear medical imaging technique producing physiological scans 18 revealing molecular processes in the body of the patient 15 reflected by migration of the uptake agent 17 preferentially to tumor tissue. An example molecular imaging uptake agent 17 is 2-deoxy-2-[fluorine-18] fluoro-D-glucose integrated with computed tomography ($^{18}$F-FDG PET/CT). This PET scanner is only one example of a physiological imaging scanner 16, however, and the invention contemplates that the physiological imaging scanners 16 may be used including functional CT or functional MRI machines or other similar devices measuring underlying metabolism of tissues.

In general, the physiological imaging scanner 16 will produce physiological scans 18 having lower spatial resolution than the high-resolution structural image scans 14 from the structural imaging scanner 12. In each case, the structural image scans 14 and agent physiological scans 18 will present dimensions of information associated with volume elements (voxels) distributed in three dimensions within a volumetric region of interest in the patient 15.

In the present invention, the patient 15 can be scanned contemporaneously in both of the structural imaging scanner 12 and physiological imaging scanner 16 which may in some cases be the same machine using different hardware or protocols. These scans will be repeated at different times throughout the course of treatment of the patient 15, for example, between sessions of treatment of the patient 15 by chemotherapy, radiation therapy, or the like.

Referring still to FIG. 1, the structural image scans 14 and agent physiological scans 18 are received by an electronic computer 22 for processing as will be described in greater detail below. Generally, the electronic computer 22 includes one or more processing units 24 communicating with a memory 26 holding data and a stored program 28 for effecting portions of the present invention. The computer 22 may communicate with a graphics display 30 for displaying color output images based on the structural image scans 14 and agent physiological scans 18 and may further communicate with user input devices 32 such as a keyboard, mouse or the like, each allowing entry of data by a user. As will be discussed in further detail below, the invention will provide an output on the display 30 indicating organ health and lesion progression or regression based on measures of agent uptake within multiple tumor and multiple organ locations in the patient 15.

Figure 2:
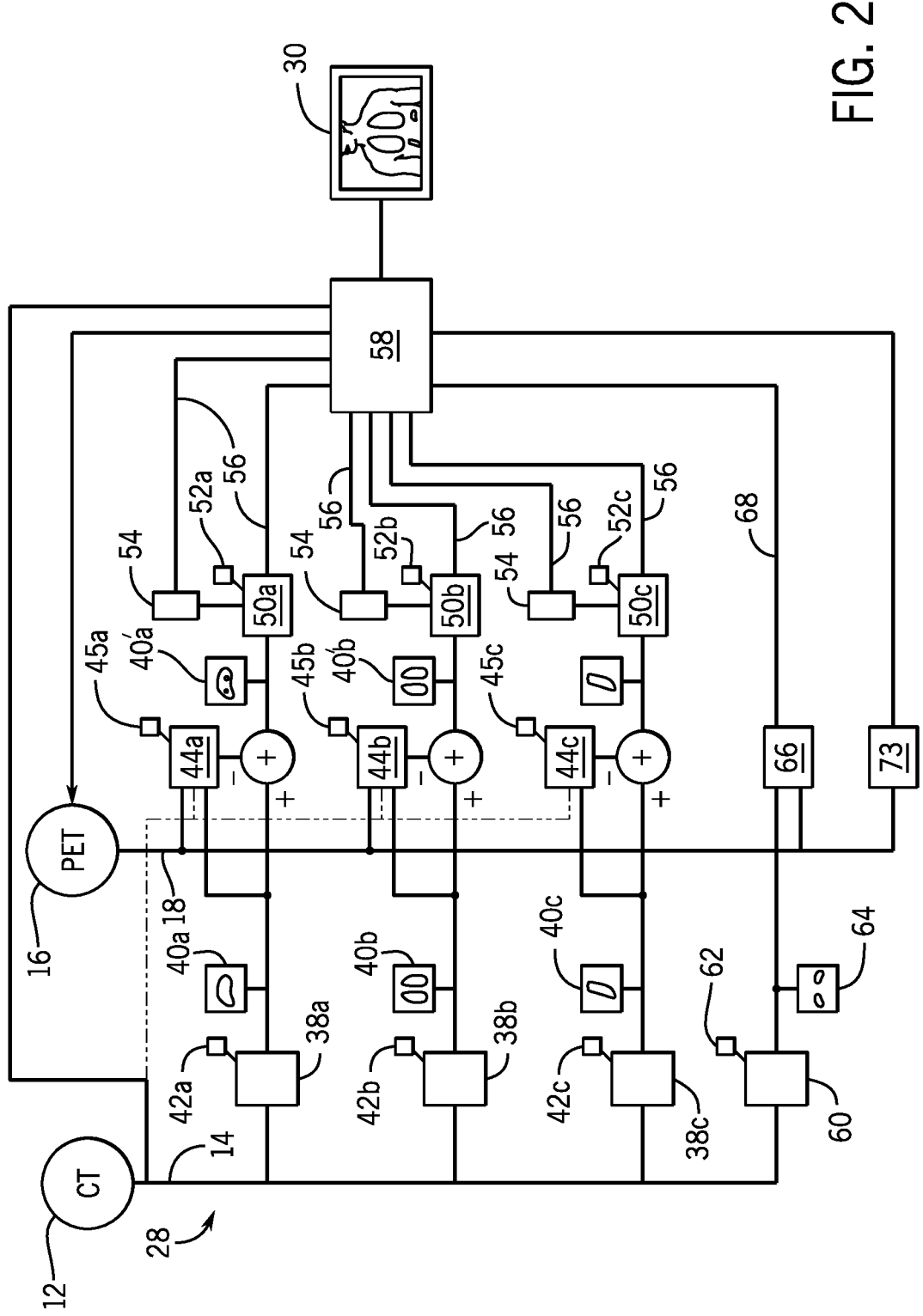
FIG. 2 is a flow block diagram showing the processing of data from the CT and PET scanner by the central processor to provide an assessment of organ health.
Figure 3:
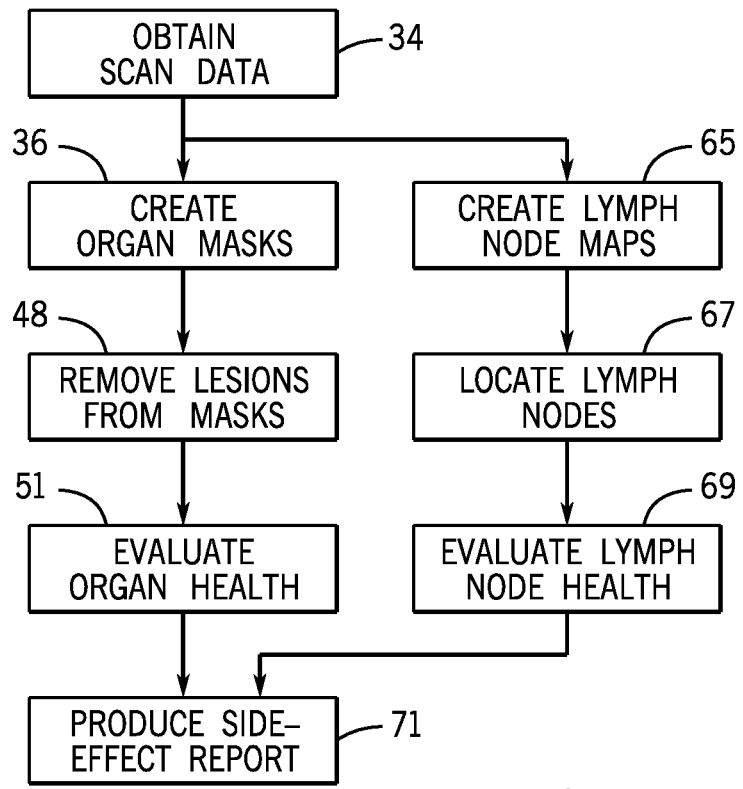
FIG. 3 is a flowchart of a program implemented by the central processor with respect to the flow block diagram of FIG. 2.

Referring now also to FIGS. 2 and 3, at a first step indicated by process block 34, the stored program 28 receives scan data obtained from the structural imaging scanner 12 and physiological imaging scanner 16 as discussed above.

Per process block 36 in FIG. 3, structural image scans 14 from the structural imaging scanner 12 are transferred to a set of segmentors 38*a*-38*b* that operate to produce masks 40*a*-40*c* isolating portions of structural image scans 14 associated with particular organs. In this respect, each of the segmentors 38 may be tuned to a particular organ, for example, the heart, lungs, brain, liver, kidneys, bones, spleen, stomach, pancreas, pharynx, larynx, blood vessels, muscles, gallbladder, intestines, lymph nodes, bone marrow, urinary bladder, etc., so that the masks 40 define specific organ volumes for each organ for the particular patient 15 but can also be easily identified to those organs. Only three segmentors 38 are shown for clarity; the number of segmentors 38 may be increased or decreased as necessary or desired to provide coverage of all organs or organ regions of interest.

In one embodiment, the segmentors 38 may be implemented as convolutional neural networks (CNN) trained, for example, using a training set of structural image scans 14 taken of different patients, pre-processed (e.g., normalized), and then segmented to identify the organs in those patients. The training set is then used to train the neural networks to produce a set of weights 42a-42c specific to the different organ types as is generally understood in the art that can produce segmentation for those organs. In one embodiment, the neural net architecture may be that of Deep Medic described by Kamnitsas K., Ledig C., Newcombe V. F., et al. in "Efficient multi-scale 3D CNN with fully connected CRF for accurate brain lesion segmentation", Med Image Anal. 2017; 36:61-78 hereby incorporated by reference. The invention contemplates that other segmenting systems may be employed that provide automatic segmentation of organ volumes. Further, although separate segmentors 38 are shown, it will be appreciated that common hardware may be used, and this processing done in sequence by changing the particular weights 42.

The information of the masks 40 for the various organs is next received by corresponding lesion identifiers 44a-44c which also receive the physiological scans 18 and/or structural scans 14 (indicated by dotted line). The lesion identifiers 44a-44c are also organ-specific having lesion identification rules 45a-45c associated with particular organs describing, for example, uptake characteristics and lesion size and shape characteristics associated with lesions in those organs to help automatically segment and identify lesions within the received masks 40 per process block 48 of FIG. 3. Techniques for automatic lesion identification may look for localized areas of excess uptake, for example, as described by US patent application 2016/0100795 assigned to the assignee of the present invention and incorporated by reference.

The output of the lesion identifiers 44 is a set of lesion volumes 46a-46c that may be subtracted (on a spatial basis) from the masks 40 to produce refined masks 40'a-40'c excluding lesion volumes.

The physiological scans 18 and the refined masks 40' are then passed to toxicity evaluator 50a-50c associated with organ-specific rules 52a-52c for the particular organ of the mask 40'. Generally, the toxicity evaluators 50 analyze the data of the physiological scans 18 limited to the area of the augmented masks 40' to provide greater sensitivity and specificity. In one embodiment, the organ-specific rules 52 may extract standardized uptake values (SUV) histogram from the physiological scans 18 within the mask 40' and store these values in a historical record 54 recording these values for successive sessions of scanning of a particular patient 15. Trending of these historical SUV values from the record 54 may then be associated with organ health. For example, the inventors have determined that for the organ of the bowel, SUV 95 defined as the 95th percentile of the bowel SUV histogram for uptake agent $^{18}$F-FDG PET/CT had a significantly higher increase from a baseline scan before treatment of the patient in patients who later experience colitis compared to those who did not. In this case, the organ-specific rule 52 for the bowel may provide that an increase in more than 40% of SUV 95 from a baseline indicates a patient who is pre-colitis (meaning likely to experience colitis) allowing for the adjustment of treatment or other measures to be adopted. A study by the inventors has indicated that the above described indication of colitis can be seen in a median of 115 days before clinical diagnosis of colitis thus providing a useful prediction of loss of organ health. This measurement has a sensitivity of 75% and a specificity of 88%. Additional rules 52 may be prepared and validated for other organs by similar empirical studies.

Each toxicity evaluator 50 using the organ-specific rules 52 may then output an organ health value 56 to a compositor 58. An example organ health value 56 may provide the relevant change in a value such as SUV 95 discussed above together with an interpretation value such as the threshold (40%) used to establish pre-colitis. These values are then used by the compositor 58 as will be discussed in more detail below. More generally, the compositor 58 combines information from each of the toxicity calculators 50 and the organ-specific rules 52. The compositor 58 also receives the raw CT structural image scans 14 as will be discussed below.

Referring still to FIGS. 2 and 3, the structural image scans 14 may also be provided to a lymph node neighborhood segmentor 60 operating in a manner similar to segmentors 38 but identifying areas of clusters of lymph nodes in the patient. The segmentor 60, in one embodiment, may also make use of a convolution neural net as described above trained using a set of structural scans manually segmented to identify the neighborhoods of lymph nodes, for example, around the base of the neck and neck, to produce a set of weights 62 for the neural net. The segment or 60 operating with the weight 62 then produces neighborhood masks 64 defining areas of clusters of lymph nodes per process block 65 of FIG. 3.

This information of the neighborhood masks 64 is sent to a lymph node evaluator 66 that uses the physiological scans 18 to identify the lymph nodes (for example, by a thresholding process or as discussed in the above cited patent) per process block 67 of FIG. 3 and determines whether they have become enlarged such as indicates a possible stressing of the lymph node system, for example, because of detectable or undetectable organ toxicity in the treatment involving immunotherapies.

Per process block 69 of FIG. 3, lymph node evaluator 66 may produce an indication 68 of lymph node enlargement, being a proxy for lymph node stress, which is also provided to the compositor 58. This indication 68, for example, may be a percent increase in lymph node size since a baseline scan indicated by agent uptake.

In addition, the structural image scans 14 and physiological scans 18 may also be used by a diseased lesion tracking circuit 73 that can provide a longitudinal monitoring of disease status and hence provide an indication of the efficacy of the primary therapy. This tracking may implement the method described in the above cited application 2016/0100795 and provides treatment information to the compositor 58.

Figure 4:
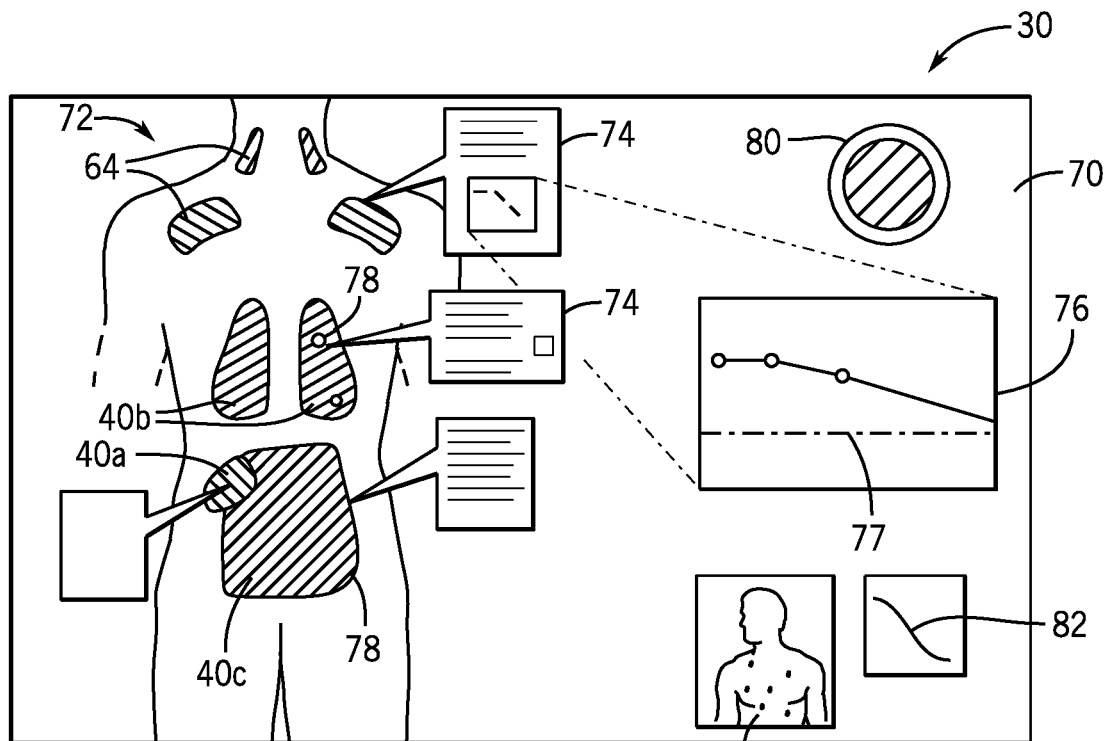
FIG. 4 is an example display produced on the display terminal of FIG. 1 using the processing of FIGS. 2 and 3.

Referring now to FIGS. 2, 3, and 4, the compositor 58 may provide an output display 70 per process block 71 providing a comprehensive overview of organ health that would be difficult or impossible for an individual relying on analysis of many different organs with different analyses standards indicated by organ-specific rules 52 and collected from various empirical studies. In one embodiment, the display 70 may provide for a scan image 72, for example, derived from the CT structural image scans 14 and depicting each of the organs 78 being analyzed highlighted using the masks of 40' and 64 developed earlier with areas of lesions 75 removed. Each of these organ images may include an annotation 74 in text and/or diagram identifying the organ and the measurements 79 that have been made, and may provide a chart 76 showing a trending of the measurement 79 of organ health and a threshold value 77 from the health value 56 per organ-specific rules 52 indicating an empirically derived threshold at which the side-effect is likely to prove limiting to the treatment. Thus, for example, for the bowel, the change in SUV 95 value may provide the measurement 79 and the 40% threshold may be displayed as threshold 77.

Each of these various health values 56 may be combined and weighted or normalized to provide a single overview indication 80 of patient organ health intended to alert the physician to possibly deteriorating situations. In cases of such alerts, the physician would then carefully review the underlying data.

In addition to monitoring patient organ health, the invention may provide an assessment of disease changes by means of a chart 82 together with a scan image 84 indicating disease locations using the data of the diseased lesion tracking circuit 73 as discussed above and with respect to cited application 2016/0100795. In this version, the invention provides a fuller view of the treatment and its effects and side effects.

It will be appreciated that the invention may provide a user interface offering the user the ability to select and alter system parameters explicitly described above or implicitly required. These can include the parameters necessary to select an organ or organs and those adding filters to control the amount and type of information provided.

The functions of the invention may be accessed or used remotely and the data collected by a imaging system can be transmitted over a communication network (e.g., secure, HIPAA compliant) to a remote computer system that analyzes the data and that results may be sent back (or elsewhere) for use.

In this regard, the invention may include database component that collect and store data from a patient or multiple patients and may use this information to modify the effective thresholds employed by the invention and/or to provide predictions or recommendations about historical outcomes that might be relevant to the particular query subject.

As used herein, the term organ refers to generally to any group of tissues adapted to perform a specific function including but not limited to the liver, the lungs, lymph nodes, the bowel, etc.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An apparatus for assessing organ health during patient treatment comprising:
    an electronic computer executing a stored program to:
    (a) receive a structural image of at least one patient organ;
    (b) receive a physiological image of the at least one organ indicating organ function;
    (c) process the structural image according to the organ function information to create a mask conforming to the at least one organ;
    (d) use the mask to select a portion of the physiological image related to the at least one organ;
    (e) apply a toxicity rule specific to the portion to provide an assessment of organ health; and
    (f) output an indication of organ health of the at least one organ based on the assessment.

2. The apparatus of claim 1 wherein the electronic computer executing the stored program further:
    processes the portion of the physiological image related to the at least one organ to identify disease lesions in the at least one organ and refines the mask to remove the lesions prior to application of the toxicity rule.

3. The apparatus of claim 2 wherein the processing of the structural image to create a mask identifies the mask to an organ type and wherein the identification of lesions in the at least one organ is according to lesion identification rules linked to the organ type.

4. The apparatus of claim 1 wherein the electronic computer executing the stored program further processes the structural image to identify a lymph node region mask; and
    wherein the lymph node region mask is used to select a portion of the physiological image related to lymph nodes; and
    wherein a lymph node activity rule is applied to the portion of the physiological image related to lymph nodes to assess the activity of the lymph nodes; and
    wherein the output also provides an indication of lymph node activity indicating activation of the lymph nodes system.

5. The apparatus of claim 1 wherein the stored program provides a set of toxicity rules linked to different organs and wherein the processing of the structural image creates a set of masks for different organs each linked to a specific organ type; and wherein the different masks are used to select different portions of the physiological image related to the different organs and the different portions are linked to specific organ types according to the mask used; and wherein the different toxicity rules are applied to different portions according to the organs linked to the toxicity rules and the organs to provide assessments of organ health for multiple different organs; and wherein the output indicates organ health for multiple organs.

6. The apparatus of claim 1 wherein the output provides a composite measure of organ health for multiple organs.

7. The apparatus of claim 1 wherein the output provides an image based on the structural image and is augmented with organ health data.

8. The apparatus of claim 1 wherein the stored program retains previous outputs indicating organ health related to previous structural images and previous physiological images to provide a display of the trending of organ health for multiple organs.

9. The apparatus of claim 1 wherein the toxicity models provide thresholds to predict organ health for multiple different organs; and wherein the output indicates predicted organ health for multiple organs.

10. The apparatus of claim 1 wherein the electronic computer further analyzes the physiological image to assess change in disease; and wherein the output provides an indication of change in disease cancerous lesions.

11. The apparatus of claim 1 wherein the physiological image is a PET scan or a functional CT or functional MRI/MRS scan.

12. The apparatus of claim 1 wherein the structural image structural image is selected from the group consisting of a CT and an MRI scan.

13. The apparatus of claim 1 wherein the electronic computer processes the structural image to create the mask describing at least one organ using machine learning trained on different organ types.

14. The apparatus of claim 1 wherein the at least one organ is the bowel and the physiological image indicates uptake of $^{18}$F-FDG.

15. The apparatus of claim 1 further including an apparatus obtaining a structural image and physiological image communicating with the electronic computer.

16. A method for assessing organ health, comprising analyzing image of information of a patient using an apparatus of any of claims 1 through 15.

17. The method of claim 16, further comprising the step of altering a treatment regimen for said patient based on said analyzing.

* * * * *